United States Patent
Splieth et al.

(10) Patent No.: US 8,900,245 B2
(45) Date of Patent: Dec. 2, 2014

(54) GLENOSPHERE INSERTER AND IMPACTOR

(75) Inventors: Roy Splieth, Central Valley, NY (US); Michael A. McGovern, Wyckoff, NJ (US); Gennaro A. Barile, Secaucus, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 72 days.

(21) Appl. No.: 13/490,737

(22) Filed: Jun. 7, 2012

(65) Prior Publication Data

US 2013/0331849 A1 Dec. 12, 2013

(51) Int. Cl.
*A61F 2/46* (2006.01)

(52) U.S. Cl.
USPC .......................................................... 606/99

(58) Field of Classification Search
USPC .............. 606/53, 81, 86 R, 91, 99, 100; 623/22.12; 403/123; 81/177.7, 177.75, 81/463; 173/90, 132; 227/147
See application file for complete search history.

(56) References Cited

U.S. PATENT DOCUMENTS

| | | | | | |
|---|---|---|---|---|---|
| 370,774 | A | * | 10/1887 | Fuller | 623/61 |
| 2,783,587 | A | * | 3/1957 | Gardel et al. | 446/379 |
| 2,807,119 | A | * | 9/1957 | Beebe | 446/317 |
| 2,968,960 | A | * | 1/1961 | Fulop | 173/48 |
| 4,916,966 | A | * | 4/1990 | Weishaupt et al. | 74/473.29 |
| 5,059,196 | A | * | 10/1991 | Coates | 606/99 |
| 5,169,399 | A | * | 12/1992 | Ryland et al. | 606/91 |
| 5,364,403 | A | * | 11/1994 | Petersen et al. | 606/91 |
| 5,431,657 | A | * | 7/1995 | Rohr | 606/91 |
| 5,540,697 | A | * | 7/1996 | Rehmann et al. | 606/91 |
| 5,584,837 | A | * | 12/1996 | Petersen | 606/91 |
| 5,733,290 | A | | 3/1998 | McCue et al. | |
| 5,735,855 | A | * | 4/1998 | Bradley | 606/86 R |
| 5,827,290 | A | * | 10/1998 | Bradley | 606/86 R |
| 5,951,195 | A | * | 9/1999 | Ruholl | 403/270 |
| 6,004,326 | A | * | 12/1999 | Castro et al. | 606/99 |
| 6,159,216 | A | | 12/2000 | Burkinshaw et al. | |
| 6,328,748 | B1 | * | 12/2001 | Hennig | 606/130 |
| 6,942,670 | B2 | | 9/2005 | Heldreth et al. | |
| 7,210,871 | B2 | * | 5/2007 | Slatter | 403/129 |
| 7,247,158 | B2 | * | 7/2007 | Harris, Jr. | 606/81 |
| 7,341,593 | B2 | * | 3/2008 | Auxepaules et al. | 606/91 |
| 7,708,739 | B2 | * | 5/2010 | Kilburn et al. | 606/86 R |
| 8,142,439 | B2 | * | 3/2012 | Parker | 606/91 |
| 8,197,484 | B2 | * | 6/2012 | Sato et al. | 606/86 B |
| 8,277,457 | B1 | * | 10/2012 | Burgi et al. | 606/91 |
| 2005/0228395 | A1 | * | 10/2005 | Auxepaules et al. | 606/91 |
| 2006/0253120 | A1 | * | 11/2006 | Anderson et al. | 606/86 |

(Continued)

*Primary Examiner* — Michael T Schaper
*Assistant Examiner* — Amy Sipp
(74) *Attorney, Agent, or Firm* — Lerner, David, Littenberg, Krumholz & Mentlik, LLP (57) ABSTRACT

An impactor for connection to a concave surface of an implant has a shaft extending along a first axis from a first end to a second end. The shaft first end includes a pivot surface surrounding an internal shaft bore. The internal bore extends along the first axis and is open at the first end and extends towards the second end about the first axis. The internal bore has a pin extending through the shaft and intersecting the bore. A resilient element is mounted in the shaft bore spaced towards the shaft second end. A post is mounted in the shaft bore along the first axis. The post has a first end engaging a threaded bore in the concave surface of the implant. The post has a second end engaging the resilient element and a slot therein slidably engaging the pin and a collar pivotally mounted on the shaft.

20 Claims, 7 Drawing Sheets

(56) References Cited

U.S. PATENT DOCUMENTS

| | | | |
|---|---|---|---|
| 2007/0123995 A1* | 5/2007 | Thelen et al. | 623/23.15 |
| 2007/0173856 A1* | 7/2007 | Parker | 606/99 |
| 2007/0225725 A1* | 9/2007 | Heavener et al. | 606/91 |
| 2009/0192515 A1* | 7/2009 | Lechot et al. | 606/91 |
| 2012/0184963 A1* | 7/2012 | Burgi et al. | 606/91 |
| 2012/0184965 A1* | 7/2012 | Burgi | 606/99 |
| 2012/0303035 A1* | 11/2012 | Geebelen | 606/91 |
| 2013/0079785 A1* | 3/2013 | Burgi | 606/91 |
| 2013/0158558 A1* | 6/2013 | Preuss et al. | 606/91 |
| 2014/0018815 A1* | 1/2014 | Kirschman | 606/99 |
| 2014/0052137 A1* | 2/2014 | Gibson et al. | 606/91 |

* cited by examiner

GLENOSPHERE INSERTER AND IMPACTOR

BACKGROUND OF THE INVENTION

The present invention relates to orthopedic implant positioners and impactors adapted to engage the convex or part-spherical outer surfaces of implants such as shoulder implants, acetabular implants and part-spherical heads for hip implants. The inserters/impactors may also be used on concave or part-spherical inner surfaces such as in acetabular cups.

Orthopedic implant positioners and impactors assist the surgeon in positioning and implanting prosthetic bearing surfaces particularly those bearing surfaces which include a threaded opening, which opening typically is a threaded central opening for accommodating a threaded post portion of the positioner/impactor. During the implantation, the surgeon will typically impact the instrument while the distal end of the positioner is in contact with the exterior or interior surface of the part-spherical implant.

U.S. Pat. No. 5,364,403 relates to an acetabular cup positioner having a resilient collar carried on the distal end of an insertion instrument which resilient collar prevents damage to the interior of an acetabular cup during impaction. The instrument has a threaded connector for engaging threads on a bore extending along the central axis of the acetabular cup. The connector is movable within the instrument and is biased towards the distal end of the instrument by a helical spring.

BRIEF SUMMARY OF THE INVENTION

The present invention relates to an inserter/impactor designed to insert and impact an orthopedic implant having a convex or part-spherical outer surface or a concave surface. The inserter/impactor has a hollow shaft with spring loaded center rod and a collar that is connected to the shaft by a ball joint. The spring loaded rod has a threaded end which allows a secure screw on connection to the implant without the impact load passing through the screw threads. The ball joint provides a swivel collar which allows a secure connection with even load distribution for both an implant with a central threaded opening to receive the threaded center rod or an implant having the threaded opening offset from its center line. Other attachment mechanism such as a spring ball detent or a bifurcated tip engaging the hole in the implant may be used.

Without the swivel collar connecting the impactor handle to the convex or substantially spherical outer surface of the implant, there would be a non-uniform impact load transfer from the collar to the implant as well as having the impact loads pass through the screw threads and potentially damaging them. This one instrument may replace two instruments respectively dedicated to the use with an on-center load axis and an off-center load axis. The implant in question may be a glenosphere for a reverse shoulder prosthetic joint system.

The inserter/impactor which can connect to a threaded bore in a convex or concave surface of an implant includes a shaft extending along a first axis from a first shaft end to a second shaft end. The shaft first end includes a pivot surface surrounding an internal bore in the shaft. The internal bore extends along the first axis. The bore is open at the shaft first end and extends towards the second end about the first axis. The internal bore has a pin extending through the shaft end and intersects the bore. The pin extends along a second axis perpendicular to the first axis. A resilient element such as a helical spring is mounted in the shaft bore spaced towards the shaft second end from the open first end of the bore. A post is mounted in the shaft bore along the first axis, the post has a threaded first end capable of engaging a threaded bore formed in a convex or concave surface of an implant. The post has a second end engaging the resilient element. The post also has a slot therein slidably engaging the pin through the shaft bore. A collar is pivotally mounted on the outer shaft pivot surface for universal angular rotation or swiveling with respect to the first axis.

The collar has a cavity with an open end surrounding the post. The open end extends around a circular opening and engages the convex or concave surface of the implant. The pivot surface on the shaft first end is part-spherical and the opening in the collar has a part-spherical surface portion resiliently engaging the part-spherical pivot surface on the shaft first end and thus can pivot such that a central axis of a cavity in the collar and the shaft first axis may form an acute angle. The collar has a part-spherical inner surface portion which includes slits extending from an inner surface of the cavity to an outer surface of the collar dividing the collar into at least two resiliently deflectable gripping portions. At least a portion of the threaded first end of the post extends beyond the end surface of the collar so that it may be threaded into the bore of the implant. The collar end surface may be circular and has a cross section formed as a section of a torous and may extend along a plane. The impactor second end may have an impaction plate thereon.

The impactor/inserter is preferably configured for connection to a concave or convex surface of an implant with the shaft extending along a first axis having either a screw or expandable collet for connecting to an opening in the concave or convex surface of the implant. This opening may extend entirely through the implant. A rod mounted in the impactor having the connector thereon, is moveable from an extended position to a retracted position in response to the shaft being impacted towards the implant. The shaft carries a collar pivotally mounted thereon surrounding the connector for angular rotation with respect to the first axis. The collar has an internal cavity having a circular end surface configured to contact the concave or convex surface of the implant. The connector rod is positioned within an internal bore formed within a first end of the shaft. A spring element, such as a coil spring, is positioned between an end wall of the bore in the shaft and an end of the rod with the spring element biasing the connection end of the rod outwardly of the end surface of the cavity in the collar. Preferably the rod connector end comprises a threaded end. The shaft end engaging the collar has a part-spherical pivot surface located on the shaft first end and surrounds the bore. The collar has a part-spherical inner surface portion resiliently engaging the part-spherical pivot surface on the shaft first end and can pivot or swivel such that a central axis of the cavity and the shaft first axis form an acute angle.

It is noted that the illustration in the drawings is only schematically and not to scale. Throughout the drawings, the same reference numerals and characters, unless otherwise stated are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures, as defined by the appended claims.

DETAILED DESCRIPTION

Referring to FIGS. 1-8, there is shown a glenosphere inserter holder/impactor generally denoted as 10 used to insert a glenosphere, such as shown in FIGS. 4-7, onto a base plate mounted on the glenoid (not shown). Inserter/impactor 10 includes a shaft 12 extending along axis 13 and having a first leading end 14 and a second end 16. Second end 16 includes an impaction plate 18 which, in connection with the glenospheres of FIGS. 4-7, is used to impact a glenosphere internal (female) conically tapered surface onto a corresponding external (male) conically tapered surface of a base plate mounted on the glenoid. A handle portion 17 is provided to hold insert/impactor 10.

Figure 1:
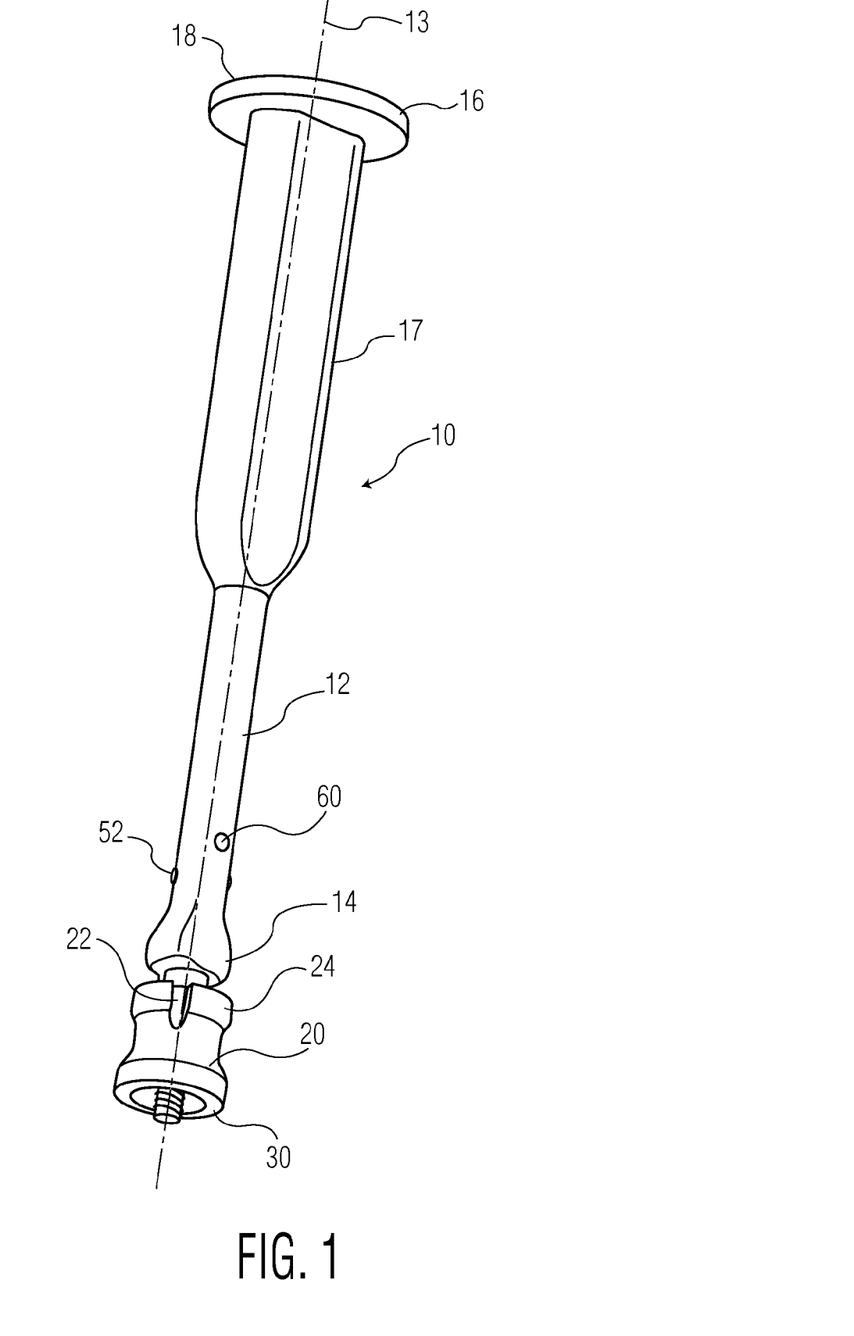
FIG. 1 is an isometric view of the prosthetic implant inserter/impactor of the present invention.
Figure 1A:
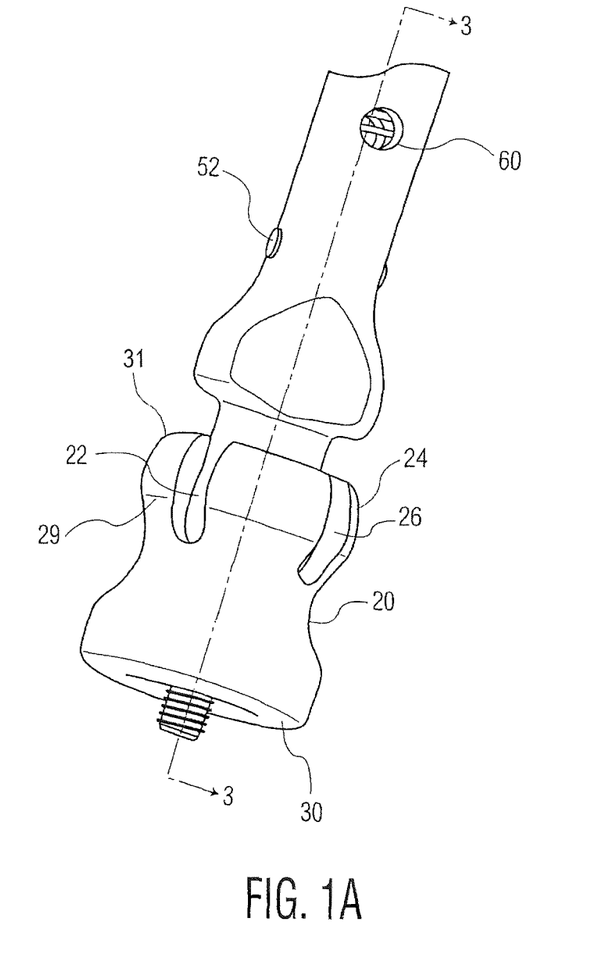
FIG. 1A is an enlarged view of the leading end of the inserter/impactor of FIG. 1.
Figure 2:
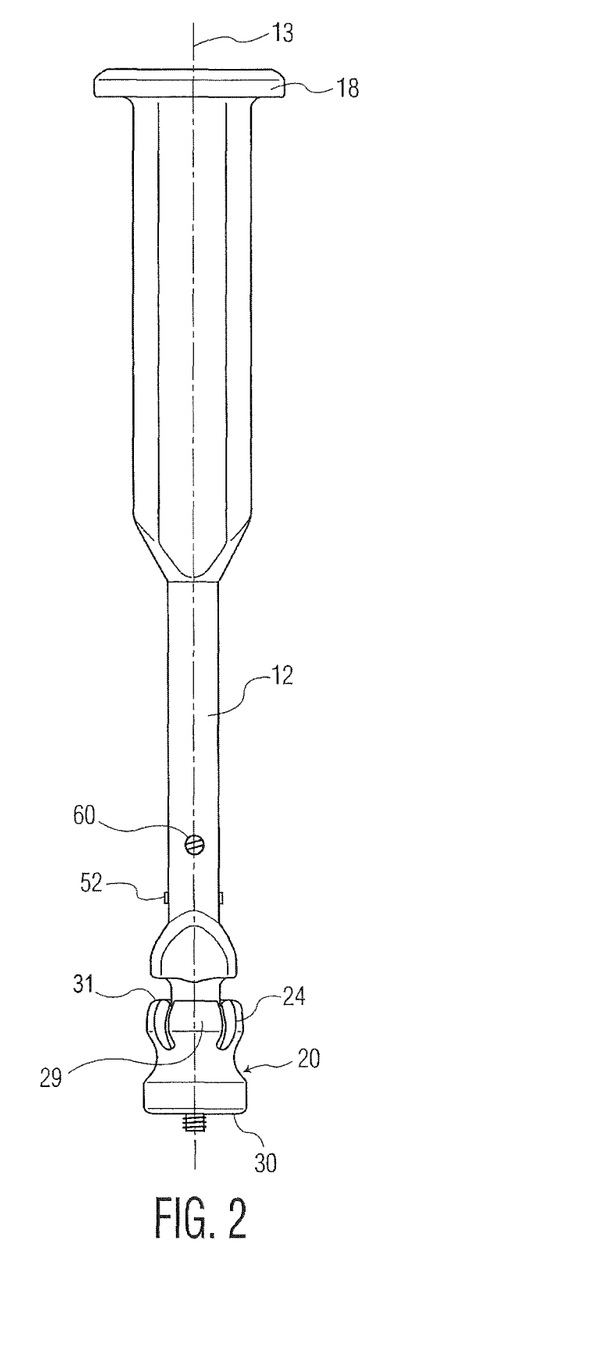
FIG. 2 is a side elevation view of the inserter/impactor of FIG. 1.
Figure 3:
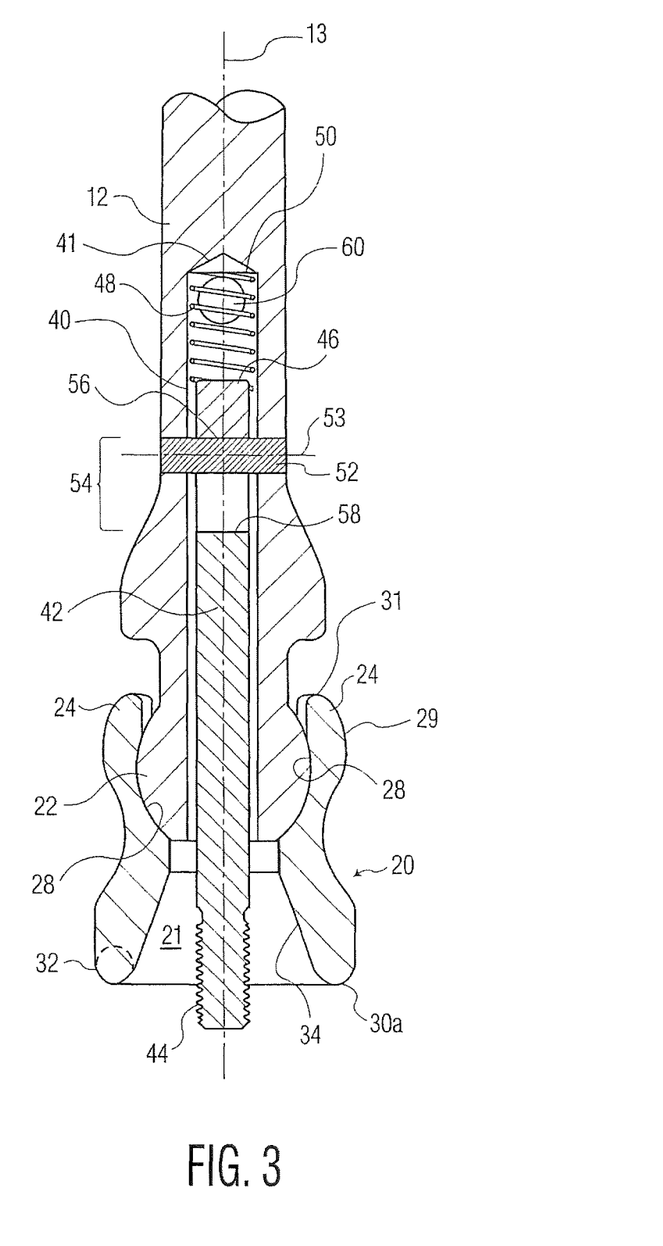
FIG. 3 is an elevation cross-sectional view of the leading end of the inserter/impactor of FIG. 1A along lines 3-3.
Figure 4:
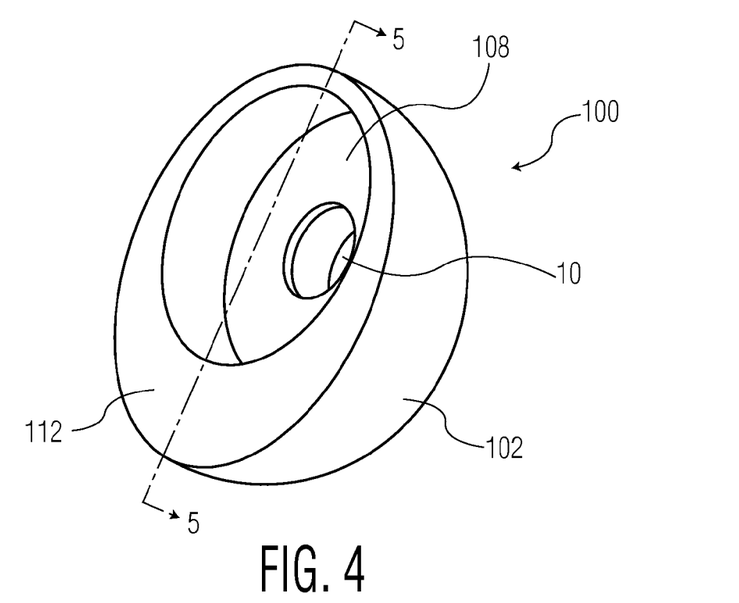
FIG. 4 is an isometric view of a prosthetic glenosphere having a cavity for receiving a baseplate which cavity is centered about an axis offset from the central axis of the glenosphere outer part-spherical surface.
Figure 5:
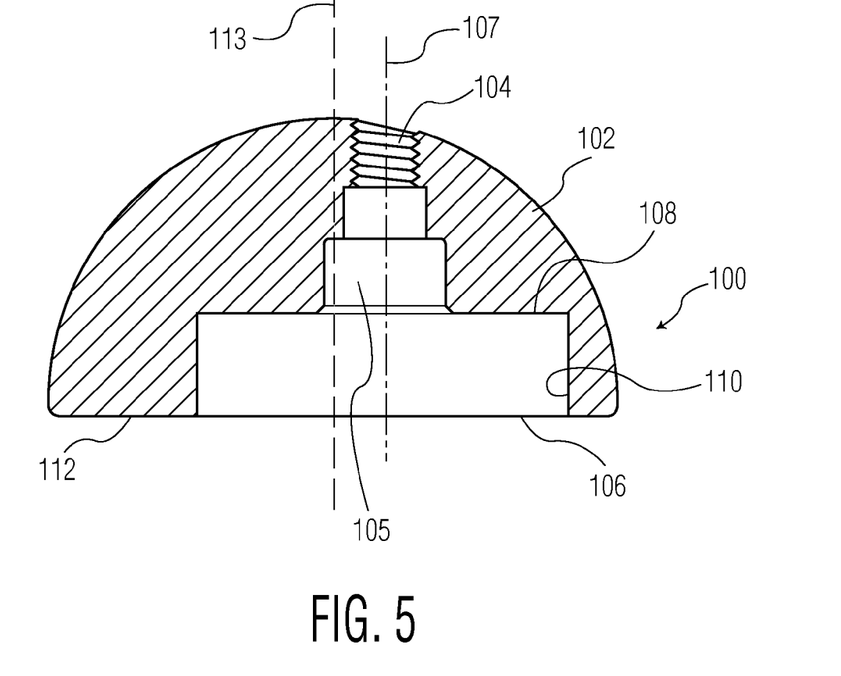
FIG. 5 is a cross-sectional view of the glenosphere of FIG. 4 along lines 5-5.

The leading end 14 of inserter/impactor 10 includes a hollow collar 20 pivotally mounted on a part-spherical portion 22 on leading end 14 of shaft 12. This is best shown in FIG. 3. Collar 20 includes at least two and preferably four resilient portions 24 which are separated by slots or slits 26. Collar 20 may have a planar end face 30 or a part-toroidal end face 30a. Collar 20 may be molded from a polymeric material such as polyethylene. Slots or slits 26 extend from an inner surface 28 of the collar 20 to an outer surface 29 thereof on an end 31 of the collar 20 mounted part-spherical portion 22. Resilient portions 24 may be resiliently sprung outwardly upon engagement with part-spherical end portion 22 so that collar 20 is maintained thereon. As best seen in FIG. 3, the inner surface of portions 24 have a part-spherical shape which, upon assembly onto end portion 22 along axis 13, forces portions 24 outwardly for resiliently receiving the outer surface of ball portion 22 with sufficient force to hold collar 20 on end part-spherical portion 22 of shaft 12.

Again referring to FIG. 3 collar 20 has an annular end surface 30a which engages the outer convex or part-spherical surface of glenosphere 100 and 200 shown in FIGS. 4-7. Surface 30a may be annular or ring-like with end 32 having a part-circular cross-section with the end 32 of the collar 20 forming a section of a torus. Inner surface 28 of collar 20 defines a cavity 21 which may have a conically tapered surface portion 34 which expands in diameter on moving along a first axis 13 of shaft 12 towards end 16 of impactor 10 a distance from axis 13 sufficient to spread any load between collar 20 and the outer convex or part-spherical surfaces of the glenosphere around a sufficiently large circumference.

Referring to FIGS. 4-7, glenospheres 100 and 200 are shown which include threaded bores 104 and 204 respectively each open to outer surfaces 102, 202 for engaging the threaded portion 44 of post 42. Threaded bores 104, 204 open into an enlarged bore portion 105, 205 and a tapered recessed area 106 and 206. Tapered recessed areas 106, 206 preferably have circumferential female conically tapered annular side walls 110, 210 designed as locking tapers for engaging a conically tapered male surface 302 on a baseplate 300 shown in FIG. 8. Recesses 106 and 206 include a generally planar upper surface 108, 208 connected by the tapered surfaces 110, 210 to a preferably planar end surface 112, 212 of glenosphere 100, 200. End surfaces 112, 212 face corresponding surfaces on the baseplate.

Glenosphere 100 differs from glenosphere 200 in that the axis of threaded bore 104 and tapered recess 106 of glenosphere 100 is along an axis 107 offset from the central axis 13 of rod 46 and shaft 12 and central axis 113 of glenosphere 100. This axial offset may be advantageous.

Figure 6:
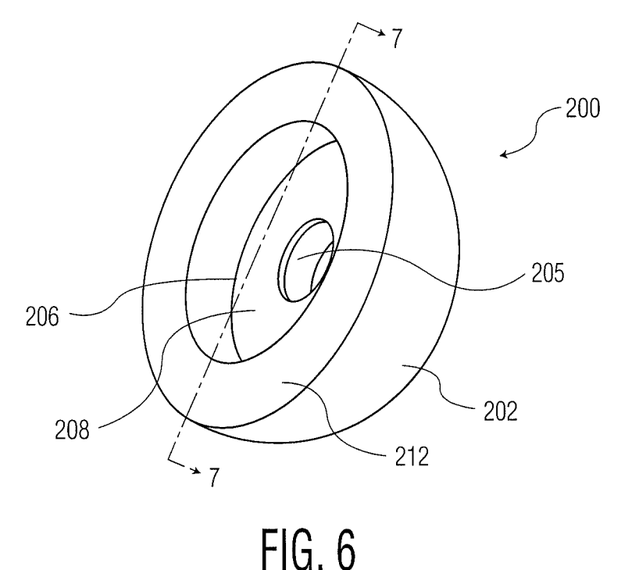
FIG. 6 is an isometric view of a glenosphere having an inner cavity for receiving a baseplate which cavity is symmetrical with the central axis of the part-spherical outer surface.
Figure 7:
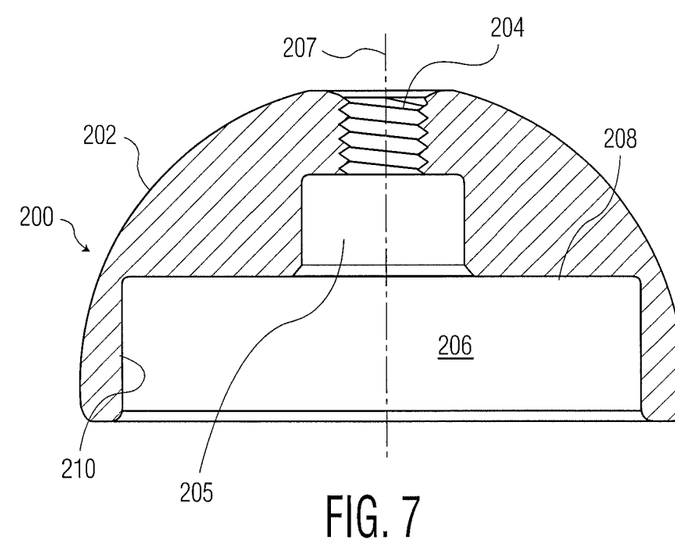
FIG. 7 is a cross-sectional view of the threaded bore and inner cavity along lines 7-7 of FIG. 6.

In glenosphere 200 the axis 207 of bore 204 and tapered recess 206 is centered on the part-spherical or convex outer surface and is thus aligned with axis 13 when assembled to inserter/impactor 10.

Again referring to FIG. 3, there is shown an internal bore 40 of shaft 12 surrounding axis 13. Bore 40 has an end 41 spaced towards second end 16 from first shaft end 14. Bore 40 houses a post or rod 42 having a partially threaded leading portion 44. Post or rod 42 has an end 46 mounted within bore 40 which engages a spring 48 which sits against a stop surface 50 of bore 40. End 46 has a slot 54 therethrough. Post 42 is held within bore 40 by a pin element 52 extending across shaft 12 along an axis 53 which is generally perpendicular to axis 13 of shaft 12 and at assembly into shaft 12, through slot 54. The sliding engagement of pin 52 within slot 54 allows post 42 to reciprocate with respect to pin 52 compressing spring 48 when an impaction hammer contacts plate 18 of second end 16 of shaft 10. The travel of post 42 is limited by ends 56 and 58 of slot 54. As shown in FIG. 3 shaft 42 is shown with threaded end 44 fully extended by the action of spring 48. A flush hole 60 is provided adjacent end 41 of bore 40 so that the bore 40, spring 48 and post 42 may be easily cleaned and sterilized.

Tapered surface 34 is angled such that collar 20 may rotate about any axis with respect to axis 13 to produce an angular offset between a central axis of cavity 21 and axis 13 of between 10 and 20 degrees. This angular offset allows collar 20 to positively engage outer surface 102 of glenosphere 100 when threaded portion 44 of rod 42 engages offset bore 104 glenosphere 100. The assembly of impactor 10 and glenosphere 200 is as described above for glenosphere 100.

Figure 8:
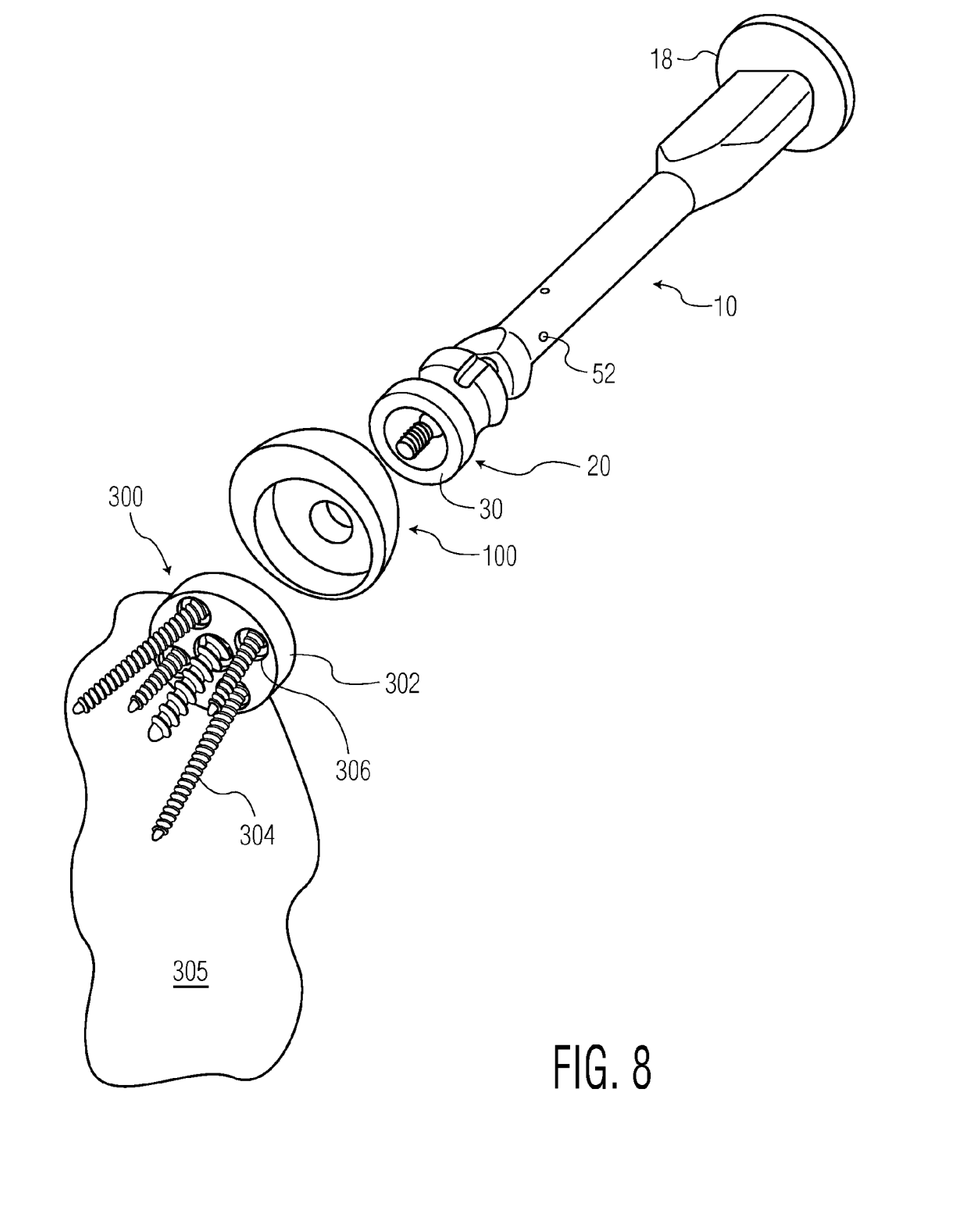
FIG. 8 is an isometric view of the inserter/impactor of FIG. 1 aligned to engage the prosthetic glenosphere of FIG. 4.

Referring to FIG. 8, there is shown an exploded view of the instrument 10 including collar 20 with glenosphere 100 and base plate 300 implanted on a glenoid or other boney structure 305 with bone screws 304. Basic plate 300 included a plurality of holes 306 for bone screws 304. Sufficient holes 306 are provided for attachment to bone 305. Once assembled, inserter/impactor 10 may be impacted by an impact hammer (not shown) contacting plate 18. This causes post 42 to act against spring 48 and absorb stresses between the threads of portion 44 and the threads of bore 104 of glenosphere 100. Shaft 12 may be provided with handle portion 17 which may be gripped and rotated so that instrument 10 may be located with respect to glenosphere 100 about axis 13. Rotation of instrument 10 about axis 13 causes shaft 12 and post 42 to rotate since torque is transferred to post 42 by pin 52 against the walls of the slot 54 in the end 46 of rod 42. Obviously rotation of shaft 12 about axis 13 in one direction couples the threaded end of portion 42 to thread into holes 104, 204 of glenosphere 100, 200 where rotation in the opposite direction allows for removing the assembly from glenosphere 100, 200 after it is locked onto base plate 300 by the engagement of locking tapers 302 and 110 or 210. Obviously, while glenosphere 100 is shown in FIG. 8, the use of inserter/impactor 10 is the same with glenosphere 200. When glenosphere 100 is used because axis 113 is offset from axis 13, collar 20 will rotate on surface 22 so that annular end surface thereof fits flush against the convex outer surface 102 of glenosphere 100. The offset between axis 13 and axis of glenosphere 100 may be up to and still allow collar 20 to fit flush on outer surface 102. When glenosphere 200 is used, the collar axis is centered about axis 13 of shaft 12.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An impactor for connection to a limited bore in a convex or concave surface of an implant comprising:
    a shaft extending along a first shaft axis from a first shaft end to a second shaft end, the first shaft end including a pivot element having an outer pivot surface surrounding an internal bore in the shaft, the internal bore in the shaft extending along the first shaft axis, the internal bore in the shaft having an opening at the first shaft end and extending towards the second shaft end about the first shaft axis, the internal bore in the shaft having a pin extending through the first shaft end and intersecting the internal bore in the shaft, the pin extending along a second axis perpendicular to the first shaft axis;
    a resilient element mounted in the internal bore in the shaft spaced towards the second shaft end from the opening of the internal bore in the shaft at the first shaft end;
    a post mounted in the internal bore in the shaft along the first shaft axis, the post having a first end capable of engaging a bore in a convex or concave surface of an implant, the post having a second end engaging the resilient element, the post having a slot therein slidably engaging the pin; and
    a collar having a cavity with an inner surface pivotally mounted on the outer pivot surface of the pivot element at the first shaft end for angular rotation with respect to the first shaft axis, the collar cavity having an open end surrounding the post defining a collar end surface, the open end of the cavity engaging the convex or concave surface of the implant in an area around the bore in the implant.

2. The impactor as set forth in claim 1 wherein the pivot surface on the first shaft end is part-spherical.

3. The impactor as set forth in claim 2 wherein the open end of the inner surface of the collar has a part-spherical surface portion engaging the part-spherical pivot surface on the first shaft end and can pivot such that a central axis of the cavity and the first shaft axis form an acute angle.

4. The impactor as set forth in claim 3 wherein the part-spherical surface portion of the cavity of the collar includes slits dividing the surface into at least two resiliently deflectable gripping portions.

5. The impactor as set forth in claim 1 wherein the post has a threaded first end and the bore on the convex or concave surface of the implant is threaded wherein at least a portion of the threaded first end of the post extends beyond the end surface of the collar.

6. The impactor as set forth in claim 5 wherein the end surface is circular and has a cross section formed as a section of a torus.

7. The impactor as set forth in claim 5 wherein the collar end surface is annular and extends in a plane.

8. The impactor as set forth in claim 1 wherein the second shaft end has an impaction plate thereon.

9. The impactor as set forth in claim 1 wherein the resilient element is a helical coil spring.

10. An impactor configured for connection to a concave or convex surface of an implant, the impactor comprising:
    a shaft having an internal bore in a first shaft end extending along a first shaft axis, the shaft having a means for connecting the impactor to the implant, the connecting means mounted in the internal bore being moveable in the internal bore from an extended position to a retracted position in response to the shaft being impacted towards the implant carried by the connecting means, wherein the shaft carries a collar having an inner surface pivotally mounted on an outwardly facing surface on the shaft first end for angular rotation with respect to the first shaft axis, the collar comprising an internal cavity defined by the collar inner surface having an end surface being configured to contact a concave or convex surface of an implant when the impactor is connected to the implant, the connecting means having an end positioned within the internal bore formed within the first shaft end, a spring element positioned between an end wall of the internal bore in the first shaft end and the end of the connecting means, the spring element biasing the connecting means outwardly of the end surface of the cavity in the collar;
    wherein the outwardly facing surface on the shaft is a part-spherical pivot surface located on the first shaft end and surrounds the internal bore in the shaft; and
    wherein the inner surface of the collar has a part-spherical surface portion resiliently engaging the part-spherical pivot surface on the first shaft end and can pivot such that a central axis of the cavity and the first shaft axis form an acute angle.

11. The impactor as set forth in claim 10 wherein the connecting means comprises a post having a threaded end.

12. The impactor as set forth in claim 11 wherein at least a portion of the threaded end of the post extends beyond the end surface of the cavity in the collar.

13. The impactor as set forth in claim 12 wherein the end surface of the collar is circular having a cross section formed as a section of a torus and surrounds the cavity in the collar.

14. The impactor as set forth in claim 12 wherein the end surface of the collar is an annular planar surface.

15. The impactor as set forth in claim 10 wherein the collar internal cavity part-spherical surface portion includes slits dividing the collar internal cavity part-spherical surface into at least two resiliently deflectable gripping portions.

16. The impactor as set forth in claim 10 wherein a shaft second end has an impaction plate thereon.

17. The impactor as set forth in claim 10 wherein the spring element is a helical coil spring.

18. An impactor configured for connection to a concave or convex surface of an implant, the impactor comprising:
    a shaft having an internal bore in a first shaft end extending along a first shaft axis, the shaft having a means for connecting the impactor to the implant, the connecting means mounted in the internal bore being moveable in the internal bore from an extended position to a retracted position in response to the shaft being impacted towards the implant carried by the connecting means, wherein the shaft carries a collar having an inner surface pivotally mounted on an outwardly facing surface on the shaft first end for angular rotation with respect to the first shaft axis, the collar comprising an internal cavity defined by the collar inner surface having an end surface being configured to contact a concave or convex surface of an implant when the impactor is connected to the implant, the connecting means having an end positioned within the internal bore formed within the first shaft end, a spring element positioned between an end wall of the internal bore in the first shaft end and the end of the connecting means, the spring element biasing the connecting means outwardly of the end surface of the cavity in the collar;

wherein the connecting means comprises a post having a threaded end; and wherein at least a portion of the threaded end of the post extends beyond the end surface of the cavity in the collar.

19. The impactor as set forth in claim 18 wherein the post has a slot extending therethrough in a direction perpendicular to the first axis and the shaft has a pin mounted thereon slidably engaging the slot.

20. An impactor configured for connection to a concave or convex surface of an implant, the impactor comprising:

a shaft having an internal bore in a first shaft end extending along a first shaft axis, the shaft having a means for connecting the impactor to the implant, the connecting means mounted in the internal bore being moveable in the internal bore from an extended position to a retracted position in response to the shaft being impacted towards the implant carried by the connecting means, wherein the shaft carries a collar having an inner surface pivotally mounted on an outwardly facing surface on the shaft first end for angular rotation with respect to the first shaft axis, the collar comprising an internal cavity defined by the collar inner surface having an end surface being configured to contact a concave or convex surface of an implant when the impactor is connected to the implant, the connecting means having an end positioned within the internal bore formed within the first shaft end, a spring element positioned between an end wall of the internal bore in the first shaft end and the end of the connecting means, the spring element biasing the connecting means outwardly of the end surface of the cavity in the collar; and wherein a shaft second end has an impaction plate thereon.

\* \* \* \* \*